(12) United States Patent
Kamakura et al.

(10) Patent No.: US 6,280,717 B1
(45) Date of Patent: Aug. 28, 2001

(54) CATION EXCHANGE RESIN PREPARATION

(75) Inventors: Minoru Kamakura; Hiromi Imai, both of Saitama (JP)

(73) Assignee: Nikken Chemicals Co., Ltd., Tokyo (JP)

(*) Notice: Subject to any disclaimer, the term of this patent is extended or adjusted under 35 U.S.C. 154(b) by 0 days.

(21) Appl. No.: 09/363,047

(22) Filed: Jul. 29, 1999

(30) Foreign Application Priority Data

Jul. 31, 1998 (JP) .................................................. 10-217328

(51) Int. Cl.⁷ .............................. A61K 31/74; A61K 9/14
(52) U.S. Cl. ................................ 424/78.1; 424/488
(58) Field of Search .................... 424/486, 78.1, 424/488, 489

(56) References Cited

U.S. PATENT DOCUMENTS

| | | |
|---|---|---|
| 4,221,778 | 9/1980 | Raghunathan . |
| 4,804,705 | 2/1989 | Pum et al. . |
| 5,167,965 | 12/1992 | Schulz . |
| 6,001,392 * | 12/1999 | Wen et al. .......................... 424/486 |

FOREIGN PATENT DOCUMENTS

| | | |
|---|---|---|
| 0192909A | 9/1986 | (EP) . |
| 0254811A | 2/1988 | (EP) . |
| 0254822A | 2/1988 | (EP) . |
| 11-72324 | 7/1989 | (JP) . |
| 2286621 | 11/1990 | (JP) . |
| 63290822 | 11/1998 | (JP) . |
| WO 9920247 | 4/1999 | (WO) . |

* cited by examiner

*Primary Examiner*—Thurman K. Page
*Assistant Examiner*—Blessing Fubara
(74) *Attorney, Agent, or Firm*—Birch, Stewart, Kolasch & Birch, LLP

(57) ABSTRACT

A cation exchange resin preparation in the dosage form of dry syrups and the like which comprises a cation exchange resin such as polystyrene calcium sulfonate and a gelleing agent such as carboxymethylcellulose sodium (CMC-Na), and may further comprises a binder such as hydroxypropyl cellulose (HPC). The preparation gelates and/or swells without disintegration for a few tens seconds to a minute or so when taken as suspensions in water or the preparation, per se. Therefore, the sandy feel in the mouth and throat, which is a problem in taking the preparation comprising a cation exchange resin alone, is reduced and the taste and easiness in oral administration are both improved. In addition, the efficacy of a cation exchange resin is never impaired through manufacturing processes

11 Claims, No Drawings

CATION EXCHANGE RESIN PREPARATION

TECHNICAL FIELD

The present invention relates to a cation exchange resin preparation used for treatment of hyperpotassemia resulting from chronic and acute renal failure. More specifically, it relates to a cation exchange resin preparation which comprises a cation exchange resin and a gelling agent, and if desired, further comprises a binder, a corrigent of taste, a disintegrator and the like.

PRIOR ART

The cation exchange resin therapy is most popular for daily potassium control in hyperpotassemia resulting from chronic and acute renal failure. However, cation exchange resin preparations are powders which hardly dissolve in water and are peculiar to the palate, and a large daily dosage of 5 to 30 g is required. At oral administration, sandy feel remains in the mouth and throat, and the unpleasant feel and the like may lead to poor compliance. This clearly indicates the necessity of a composition of a cation exchange resin preparation with better feel of oral administration compared to conventional cation exchange resin preparations.

In order to improve the feel of oral administration of a strongly basic anion exchange resin (e.g. cholestyramine), there have been known so far a method of obtaining a dry syrup by fixing an anion exchange resin to a large amount of gum such as hydroxypropyl methylcellulose and methylcellulose (see, for example, Japanese Patent Unexamined Publication (KOKAI) No. (Sho) 63-290822/1988 and No. (Hei) 1-172324/1989), and a method of obtaining a tablet using a hydrophobic substance such as higher fatty acids, their metal salts or glycerol esters, and wax, together with a binder such as hydroxypropyl cellulose and methylcellulose (see, for example, Japanese Patent Unexamined Publication (KOKAI) No. (Hei) 2-286621/1990). However, these methods are limited to those for improving the feel of oral administration of anion exchange resins. In addition, the aforementioned methods require a large quantity of hydrophobic substances and the like to improve the feel of administration of the ion exchange resin preparations. This may cause problems in that manufacturing methods are inconvenient and doses are too large.

DISCLOSURE OF THE INVENTION

Accordingly, an object of the present invention is to provide a composition of an ion exchange resin preparation which can be prepared conveniently and give excellent feel of oral administration, although it contains only a small amount of additives such as a gelling agent. Another object of the present invention is to provide preparations which can easily be dispersed and suspended in water by stirring for only a few seconds before oral administration and will not cause aggregation for a while after the suspending. Further object of the present invention is to provide preparations which can rapidly be re-dispersed by stirring in a few seconds even after precipitation is formed by leaving the suspension to stand for a while.

The present inventors conducted various studies to solve the foregoing problems and found that preparations, which were obtained by kneading a small amount of a gelling agent and, if desired, a binder and the like into a cation exchange resin and extruding the mixture for granulation, achieved remarkably easier feel of oral administration compared to preparations consisting solely of a cation exchange resin. The present invention was achieved on the basis of these findings.

The present invention thus relates to a cation exchange resin preparation which comprises a cation exchange resin and a gelling agent, preferably, it relates to the cation exchange resin preparation which further comprises a binder, a disintegrator and the like. According to a preferred embodiment, there is provided the cation exchange resin preparation comprising a cation exchange resin, a gelling agent, and a binder, whose dosage form is granules, powders, or dry syrups, and more preferably in the form of dry syrups.

According to further preferred embodiments, the cation exchange resin may be a polystyrene sulfonic acid metal salt such as, for example, a polystyrene calcium sulfonate or a polystyrene sodium sulfonate. The gelling agent may be one or more substances selected from the group consisting of carboxymethylcellulose sodium (CMC-Na), hydroxypropyl methylcellulose (HPMC) and methylcellulose (MC), and the binder may be one or more substances selected from the group consisting of dextrin, crystalline cellulose, hydroxypropyl cellulose (HPC), and ethyl cellulose (EC).

According to particularly preferred embodiments, the gelling agent is carboxymethylcellulose sodium (CMC-Na), and the binder is hydroxypropyl cellulose (HPC). Most preferably, the cation exchange resin is a polystyrene calcium sulfonate, the gelling agent is carboxymethylcellulose sodium (CMC-Na), and the binder is hydroxypropyl cellulose (HPC).

BEST MODE FOR CARRYING OUT THE INVENTION

The present invention will be explained in detail.

The cation exchange resin preparation of the present invention may preferably be in the dosage form of granules, powders, or dry syrups, and dry syrups are particularly preferred.

As the cation exchange resin, polystyrene sulfonic acid metal salts, particularly a polystyrene calcium sulfonate or a polystyrene sodium sulfonate, are preferred. Particle size of the cation exchange resin may be from 5 to 500 $\mu$m, and in particular, 50 to 100 $\mu$m is preferred.

As the gelling agent used in the present invention, examples include carboxymethylcellulose sodium (CMC-Na, carmellose sodium), hydroxypropyl methylcellulose (HPMC), methylcellulose (MC), croscarmellose sodium (CCMC-Na) and the like. Preferable examples include CMC-Na, HPMC and MC, and CMC-Na is particularly preferred. The gelling agent is used in an amount of from 0.5 to 20% based on the total weight of the preparation of the present invention, preferably from 1 to 10%, and more preferably from 1 to 5%.

As the binder, examples include dextrin, crystalline cellulose, hydroxypropyl cellulose (HPC), ethylcellulose (EC) and the like, and particularly HPC. The binder is used in an amount of from 0.1 to 20% based on the total weight of the preparation of the present invention, preferably from 1 to 10%.

The preparations of the present invention can be added with, if desired, a disintegrator such as carboxymethylcellulose (CMC) and carboxymethylcelulose calcium (CMC-Ca) in addition to the gelling agent and the binder.

If desired, a small amount of a corrigent of taste may be used in the preparations of the present invention to higher sweetness and/or improve taste. Examples include, for example, fructose, xylitol, purified sucrose, glucose, maltose, D-mannitol, stevioside, glycyrrhizic acid, a salt of glycyrrhizic acid, and thaumatin, or artificial sweeteners such as, for example, aspartame, saccharin, and sodium saccharin. These natural and artificial corrigent of taste are well-known, and any of them may suitably used for the present invention. Among them, aspartame is particularly preferred when the preparation is administered to patients with renal failure and/or diabetes. The corrigent of taste may be used alone or in combination of two or more.

Also if desired, a small amount of corrigent of smell may be used in the preparations of the present invention to increase flavor and/or mask smells. Examples include, for example, flavors of mixed fruit, pineapple, strawberry, orange, grape, raspberry, apricot, lemon, lime, cherry, glycyrrhiza, spearmint, peppermint, chocolate, coffee, banana, vanilla and the like. The corrigent of smell may be used alone or in combination of two of more.

The cation exchange resin preparation of the present invention can be manufactured by kneading a small amount of the gelling agent, and optionally further additives such as a binder and a disintegrator, into the cation exchange resin; extruding the mixture for granulation; and then drying to obtain granules; and if desired, adding a small amount of the corrigent of taste and/or smell. In addition, the cation exchange resin preparation of the present invention can be prepared by the processes of kneading granulation, fluid-bed granulation, or fluid-bed granulation by rolling and stirring in addition to the extruding granulation process. The reparation can also be manufactured by mixing powders of the cation exchange resin, the gelling agent, the binder and the like without granulation.

EXAMPLES

The present invention will be explained more specifically with reference to examples. However, the scope of the present invention is not limited to the following examples.

Example 1

(Preparation of Granules)

300 g of polystyrene calcium sulfonate of Japanese Pharmacopoeia, a cation exchange resin having particle size of approximately 60 µm, and 30 g of carboxymethylcellulose sodium (CMC-Na) were added with 250 g of water, and the mixture was kneaded using a Shinagawa-type universal mixing machine to prepare a paste. The resulting paste was dried at 60° C. for 12 hours, and the crude granules after the drying were sized by using an oscillating granulator equipped with a 13 mesh (1.29 mm) screen (die) to prepare granules.

Reference Examples 1 to 4

Granules were prepared in a similar manner to Example 1, except that 30 g of gelatin (Reference Example 1), dextrin (Reference Example 2), Carbopol 947NF (trade name; Chugai Boeki; carboxyvinyl polymer) (Reference Example 3) or powdery agar (Reference Example 4), respectively, was used instead of 30 g of CMC-Na.

Test Example 1

Using the granules obtained in Example 1 and Reference Examples 1 to 4, evaluations were carried out as to granulating properties (easiness for forming granules and oscillating property) in the process of the granule preparations and the feel of oral administration when the resulting granules, per se, or suspensions in 10 times volume of water were administered.

As a result, the granules of Example 1 were excellent both in the granulating properties and the feel of oral administration. In contrast, the granules of Reference Examples 1 and 4 were bad both in the granulating properties and the feel of oral administration. The granules of Reference Example 2 were good in the granulating properties, but bad in the feel of oral administration. The granulates of Reference Example 3 were bad in the granulating properties and slightly improved in the feel of oral administration.

The feel of oral administration was evaluated using 10 panelists based on 3 criteria, i.e., bad: no improvement in the feel of oral administration compared to the cation exchange resin as the low material; slightly good: a little improvement in easy feel of administration; and good: remarkable improvement in easiness of oral administration. A criteria in majority was used as a result of evaluation.

Example 2

(Preparation of Dry Syrup 1)

300 g of a cation exchange resin (polystyrene calcium sulfonate of Japanese Pharmacopoeia) and 5 g of CMC-Na and 20 g of hydroxypropyl cellulose of medium viscosity (HPC-M) were added with 250 g of water, and the mixture was kneaded using a Shinagawa-type universal mixing machine to prepare a paste. The resulting paste was then extruded for granulation using a basket-type granulator equipped with a 0.6 mm screen (die) to prepare crude granules. After drying, the crude granules were sized using an oscillating granulator equipped with a 32 mesh (0.48 mm) screen (die) to prepare core granules (cylindrical granules). The core granules were added with 0.45 g or aspartame and 0.2 g of Metholose SM-100 (trade name; Shin-etsu Kagaku; methylcellulose) in form of powders, and then the mixture was mixed using a Bohle container mixer to obtain Dry Syrup 1 comprising the cation exchange resin. The composition of Dry Syrup 1 is shown in Table 1.

TABLE 1

| Composition of Dry Syrup 1 | |
|---|---|
| Substance | parts by wt. |
| Cation exchange resin | 100 |
| CMC-Na | 1.67 |
| HPC-M | 6.67 |

TABLE 1-continued

Composition of Dry Syrup 1

| Substance | parts by wt. |
|---|---|
| Aspartame | 0.15 |
| Metholose SM-100 | 0.07 |
| Total | 108.56 |

Example 3
(Preparation of Dry Syrup 2)

In 200 g of a water/methanol mixed solution (1:1, w/w), 1 g of aspartame and 4.45 g of Metholose SM-100 were dissolved to prepare a coating solution. The core granules (325 g) prepared in Example 2 were coated with 180 g of the coating solution using a fluid-bed granulator to obtain Dry Syrup 2 comprising the cation exchange resin. The composition of Dry Syrup 2 is shown in Table 2.

TABLE 2

Composition of Dry Syrup 2

| Substance | parts by wt. |
|---|---|
| Cation exchange resin | 100 |
| CMC-Na | 1.67 |
| HPC-M | 6.67 |
| Aspartame | 0.30 |
| Metholose SM-100 | 1.37 |
| Total | 110.01 |

Test Example 2

Dry Syrup 1 and 2 obtained in Example 2 and 3, and a cation exchange resin (polystyrene calcium sulfonate of Japanese Pharmacopoeia) as a control were subjected to measurement of sedimentation velocity by using TURBISCAN MA2000 (FORMAL ACTION) as a measuring apparatus for the stability of a solution. The results are shown in Table 3. The sedimentation velocity of the preparations obtained by the present invention (dry syrups) was highly reduced compared to the conventional preparation (the cation exchange resin), which indicates remarkable improvements of dispersibility.

TABLE 3

| Substance | Sedimentation velocity (mm/min) |
|---|---|
| Cation exchange resin | 2.4743 |
| Dry Syrup 1 | 0.1527 |
| Dry Syrup 2 | 0.1675 |

Test Example 3

Dry Syrup 2 obtained in Example 3 and a cation exchange resin (polystyrene calcium sulfonate of Japanese Pharmacopoeia) as a control were subjected to sensory tests using 53 panelists applied by two administration methods, i.e., taking the drugs after suspended in water and taking the drugs, per se. Each panelist took drugs in four manners: 3.7 g of the dry syrup (3.3 g of the cation exchange resin) with 33 mL of water or 3.3 g of the cation exchange resin with 33 mL of water, each by taking the drugs after suspended in water or taking the drugs, per se. $\hat{1}$ Taste, $\hat{2}$ easiness in oral administration, and $\hat{3}$ improved degree (a degree of improvement of the dry syrup compared to the cation exchange resin) were evaluated based on 9 grades from −4 to +4. The results of score distribution (the number of panelists×score) are shown in Table 4, and those of the sensory tests (the sum of the score distribution) in Table 5.

As to the age of the panelists, 53 panelists composed of 30 of the twenties, 6 of the thirties, 8 of the forties, and 9 of the fifties. In Table 4, test items with the sum of less than 53 indicate the existence of one or more panelists giving no answer.

TABLE 4

| Dosage form | Method of administration | Evaluation item | +4 | +3 | +2 | +1 | 0 | −1 | −2 | −3 | −4 | Sum |
|---|---|---|---|---|---|---|---|---|---|---|---|---|
| Cation exchange resin | Suspension | Taste | 0 | 1 | 0 | 2 | 12 | 9 | 14 | 9 | 6 | 53 |
| | | Easiness in taking | 0 | 1 | 4 | 3 | 5 | 8 | 15 | 10 | 7 | 53 |
| | Drug, per se | Taste | 0 | 0 | 1 | 2 | 8 | 11 | 5 | 9 | 13 | 49 |
| | | Easiness in taking | 0 | 1 | 1 | 1 | 6 | 7 | 8 | 12 | 14 | 50 |
| Dry syrup | Suspension | Taste | 0 | 7 | 11 | 14 | 6 | 9 | 3 | 2 | 1 | 53 |
| | | Easiness in taking | 1 | 7 | 10 | 5 | 11 | 6 | 7 | 3 | 2 | 52 |
| | | Improved degree | 6 | 10 | 9 | 18 | 3 | 4 | 1 | 2 | 0 | 53 |
| | Drug, per se | Taste | 2 | 3 | 15 | 14 | 11 | 5 | 3 | 0 | 0 | 53 |
| | | Easiness in taking | 2 | 6 | 6 | 4 | 9 | 9 | 6 | 8 | 2 | 52 |
| | | Improved degree | 7 | 15 | 9 | 7 | 1 | 7 | 3 | 1 | 0 | 50 |

TABLE 5

Result of Sensory tests

| Dosage form | Method of taking | Taste | Easiness in taking | Improved degree |
|---|---|---|---|---|
| Cation exchange resin | Suspension | −83 | −82 | |
| | Drug, per se | −96 | −109 | |
| Dry syrup | Suspension | +32 | +13 | +78 |
| | Drug, per se | +50 | −11 | +82 |

From the results of the sensory tests, it can be understood that the preparations obtained by the present invention were improved both in the taste and the easiness in oral administration compared to the conventional preparation.

Example 4
(Preparation of Dry Syrup 3)

Using polystyrene sodium sulfonate of Japanese Pharmacopoeia as a cation exchange resin, Dry Syrup 3 of cation exchange resin were prepared in the same manner as Example 2.

The resulting dry syrup was improved in the taste and the easiness in oral administration in the same manner as Dry Syrup 2 obtained in Example 3.

The cation exchange resin preparations of the present invention gelate and/or swell without disintegration approximately for a few tens seconds to a minute when taken as suspensions in water or as the preparation, per se. Therefore, sandy feel in the mouth and throat, which is a problem in taking a preparation comprising a cation exchange resin alone, is reduced and taste and easiness in oral administration are both improved. In addition, in the preparations of the present invention, efficacy of a cation exchange resin will not be impaired through manufacturing processes. Moreover, since the gelling agent, the binder and the like used in the present invention are natural or artificial polymers, the preparations can reduce constipation tendency caused as an adverse effect by most of ion exchange resin preparations.

What is claimed is:

1. A cation exchange resin preparation which comprises a cation exchange resin and carboxymethylcellulose sodium (CMC-Na) as a gelling agent, wherein said gelling agent is present in an amount ranging from 0.5 to 20% by weight based on the total weight of the preparation.

2. The cation exchange resin preparation according to claim 1, which further comprises a binder.

3. The cation exchange resin preparation according to claim 1, wherein the dosage form is granules, powders, or dry syrups.

4. The cation exchange resin preparation according to claim 1, wherein the cation exchange resin is a polystyrene sulfonic acid metal salt.

5. The cation exchange resin preparation according to claim 1, wherein the binder is one or more substances selected from the group consisting of dextrin, crystalline cellulose, hydroxypropyl cellulose (HPC), and ethyl cellulose (EC).

6. The cation exchange preparation according to claim 1, wherein said gelling agent is present in an amount ranging from 1 to 10% by weight based on the total weight of the preparation.

7. The cation exchange preparation according to claim 1, wherein said gelling agent is present in an amount ranging from 1 to 5% by weight based on the total weight of the preparation.

8. The cation exchange resin preparation according to claim 2, wherein the binder is hydroxypropyl cellulose (HPC).

9. The cation exchange resin preparation according to claim 2, wherein the cation exchange resin is polystyrene calcium sulfonate and the binder is hydroxypropyl cellulose (HPC).

10. The cation exchange resin preparation according to claim 9, wherein the dosage form is dry syrups.

11. The cation exchange resin preparation according to claim 3, wherein the cation exchange resin is a polystyrene calcium sulfonate or a polystyrene sodium sulfonate.

* * * * *